United States Patent
Marsh

(10) Patent No.: US 9,433,728 B2
(45) Date of Patent: Sep. 6, 2016

(54) VALVELESS PHARMACEUTICAL INFUSION SYSTEM

(71) Applicant: MEDRAD, INC., Indianola, PA (US)

(72) Inventor: Charles Marsh, Cranberry Township, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 702 days.

(21) Appl. No.: 13/783,213

(22) Filed: Mar. 1, 2013

(65) Prior Publication Data

US 2014/0249349 A1 Sep. 4, 2014

(51) Int. Cl.
*A61M 5/142* (2006.01)
*A61M 5/00* (2006.01)

(52) U.S. Cl.
CPC ......... *A61M 5/14232* (2013.01); *A61M 5/007* (2013.01)

(58) Field of Classification Search
CPC ............. A61M 5/007; A61M 5/1407; A61M 5/1408; A61M 5/142; A61M 5/14232; A61M 2005/14208
See application file for complete search history.

(56) References Cited

U.S. PATENT DOCUMENTS

| | | |
|---|---|---|
| 4,401,108 A | 8/1983 | Galkin et al. |
| 4,409,966 A | 10/1983 | Lambrecht et al. |
| 4,472,403 A | 9/1984 | Trijzelaar et al. |
| 4,562,829 A | 1/1986 | Bergner |
| 4,585,009 A | 4/1986 | Barker et al. |
| 4,883,459 A | 11/1989 | Calderon |
| 4,902,282 A | 2/1990 | Bellotti et al. |
| 5,059,173 A * | 10/1991 | Sacco ................. A61M 5/1408 604/246 |
| 5,383,858 A | 1/1995 | Reilly et al. |
| 5,472,403 A | 12/1995 | Cornacchia et al. |
| 5,514,071 A | 5/1996 | Sielaff, Jr. et al. |
| 5,520,653 A | 5/1996 | Reilly et al. |
| 5,918,443 A | 7/1999 | Phillips |
| 5,927,351 A | 7/1999 | Zhu et al. |
| 5,947,890 A | 9/1999 | Spencer et al. |
| 6,017,318 A | 1/2000 | Gauthier et al. |
| 6,267,717 B1 | 7/2001 | Stoll et al. |
| 6,442,418 B1 | 8/2002 | Evans, III et al. |
| 6,450,936 B1 | 9/2002 | Smith, III et al. |

(Continued)

FOREIGN PATENT DOCUMENTS

| | | |
|---|---|---|
| IT | RM 96A000148 | 3/1996 |
| WO | 0137904 A2 | 5/2001 |
| WO | 2011/153457 | 12/2011 |

OTHER PUBLICATIONS

The International Search Report and Written Opinion mailed Jun. 2, 2014 from corresponding PCT Application No. PCT/US2014/018239.

(Continued)

*Primary Examiner* — Kami A Bosworth
(74) *Attorney, Agent, or Firm* — Joseph L. Kent; David Schramm; James R. Stevenson

(57) ABSTRACT

A valveless pharmaceutical infusion system for delivery of a pharmaceutical, such as a radiopharmaceutical, is described. The device may include two or more roller pumps, a fluid path set including a confidence, and a measuring device for measuring a property of the pharmaceutical. Methods for delivering a pharmaceutical, such as a radiopharmaceutical, using a valveless pharmaceutical infusion system are also describe.

16 Claims, 6 Drawing Sheets

(56) References Cited

U.S. PATENT DOCUMENTS

| | | |
|---|---|---|
| 6,471,674 B1 | 10/2002 | Emig et al. |
| 6,491,656 B1 | 12/2002 | Morris |
| 6,520,930 B2 | 2/2003 | Critchlow et al. |
| 6,767,319 B2 | 7/2004 | Reilly et al. |
| 7,018,363 B2 | 3/2006 | Cowan et al. |
| 7,204,797 B2 | 4/2007 | Reilly et al. |
| 7,905,861 B2 | 3/2011 | Rhinehart et al. |
| 8,029,454 B2 | 10/2011 | Kelly et al. |
| 8,198,599 B2 | 6/2012 | Bouton et al. |
| 8,454,561 B2 | 6/2013 | Uber, III et al. |
| 2003/0040700 A1 | 2/2003 | Hickle et al. |
| 2007/0038191 A1 | 2/2007 | Burbank et al. |
| 2007/0123838 A1 | 5/2007 | Bernard et al. |
| 2008/0177126 A1 | 7/2008 | Tate et al. |
| 2010/0063481 A1 | 3/2010 | Hoffman et al. |
| 2011/0021905 A1 | 1/2011 | Patrick et al. |
| 2011/0132482 A1 | 1/2011 | Patrick et al. |
| 2011/0178359 A1 | 7/2011 | Hirschmann et al. |
| 2013/0123567 A1 | 5/2013 | Agamaite et al. |
| 2014/0046295 A1 | 2/2014 | Uber, III et al. |

OTHER PUBLICATIONS

The International Preliminary Report on Patentability mailed Sep. 11, 2015 from corresponding PCT Application No. PCT/US2014/018239.

The International Preliminary Report on Patentability and Written Opinion and International Search Report mailed May 21, 2015 from corresponding PCT Application No. PCT/US2013/044038.

* cited by examiner

VALVELESS PHARMACEUTICAL INFUSION SYSTEM

CROSS-REFERENCE TO RELATED APPLICATIONS

Not Applicable

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

Radiopharmaceuticals are provided by manufacturers in numerous concentrations in sterilized containers (such as glass bottles or plastic packages) ranging incrementally in size from 20 ml to 200 ml. These containers are generally designed for a single use in which once a container is opened for a patient, then it is used for that patient only. The radiopharmaceutical is, generally, aspirated from such containers via a syringe pump used to inject the radiopharmaceutical, and any radiopharmaceutical remaining in the container is discarded to prevent infection with potentially contaminated contrast. The medical staff is faced with the task of choosing an appropriately sized container to assure an adequate injection while minimizing discarded radiopharmaceutical. Time consuming procedures are required to reload the syringe if more radiopharmaceutical is required than originally calculated, and expensive waste results if only a portion of a filled syringe is injected.

SUMMARY OF THE INVENTION

In an embodiment, the present disclosure provides a device for delivering a pharmaceutical. The device comprises two or more roller pumps and a fluid path set reversibly attached to the device. The fluid path set may comprise a first tubing section fluidly connecting a pharmaceutical source to a confluence, a second tubing section fluidly connecting a source of medical fluid to the confluence, and a third tubing section fluidly connecting the confluence to an exit port. Flow of fluid through the first tubing section may be controlled by a first roller pump and flow of fluid through the second tubing section may be controlled by a second roller pump. In certain embodiments, the pharmaceutical may be a radiopharmaceutical. In certain embodiments, the device may further comprise a measuring device, such as an activity measuring device, to measure one or more properties of the pharmaceutical. In certain embodiments, the device may comprise a fourth tubing section fluidly connecting the third tubing section or portion thereof to a waste receptacle. In certain embodiments the device may further comprise one or more by-pass tubing sections as described herein.

In an embodiment, the present disclosure provides a method for delivering a pharmaceutical. The method comprises activating a first roller pump to introduce a medical fluid into a confluence, activating a second roller pump to introduce a pharmaceutical into the confluence, and delivering the medical fluid and the pharmaceutical to a patient. In certain embodiments the pharmaceutical may be a radiopharmaceutical. In certain embodiments, the method may further comprise determining a dose of radiation in the radiopharmaceutical before delivering the medical fluid and the radiopharmaceutical to the patient.

In another embodiment, the present disclosure provides a method for delivering a radiopharmaceutical comprising identifying a dose of radiopharmaceutical to be delivered to a patient, introducing a first quantity of the radiopharmaceutical into a measuring devices, determining an activity level of the first quantity of the radiopharmaceutical, and introducing one or more additional quantities of the radiopharmaceutical into the measuring device to make a total quantity of radiopharmaceutical having the identified dose. In certain embodiments, the method may further comprise delivering the total quantity of radiopharmaceutical having the identified dose to a patient.

DESCRIPTION OF DRAWINGS

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

DETAILED DESCRIPTION

Figure 1:
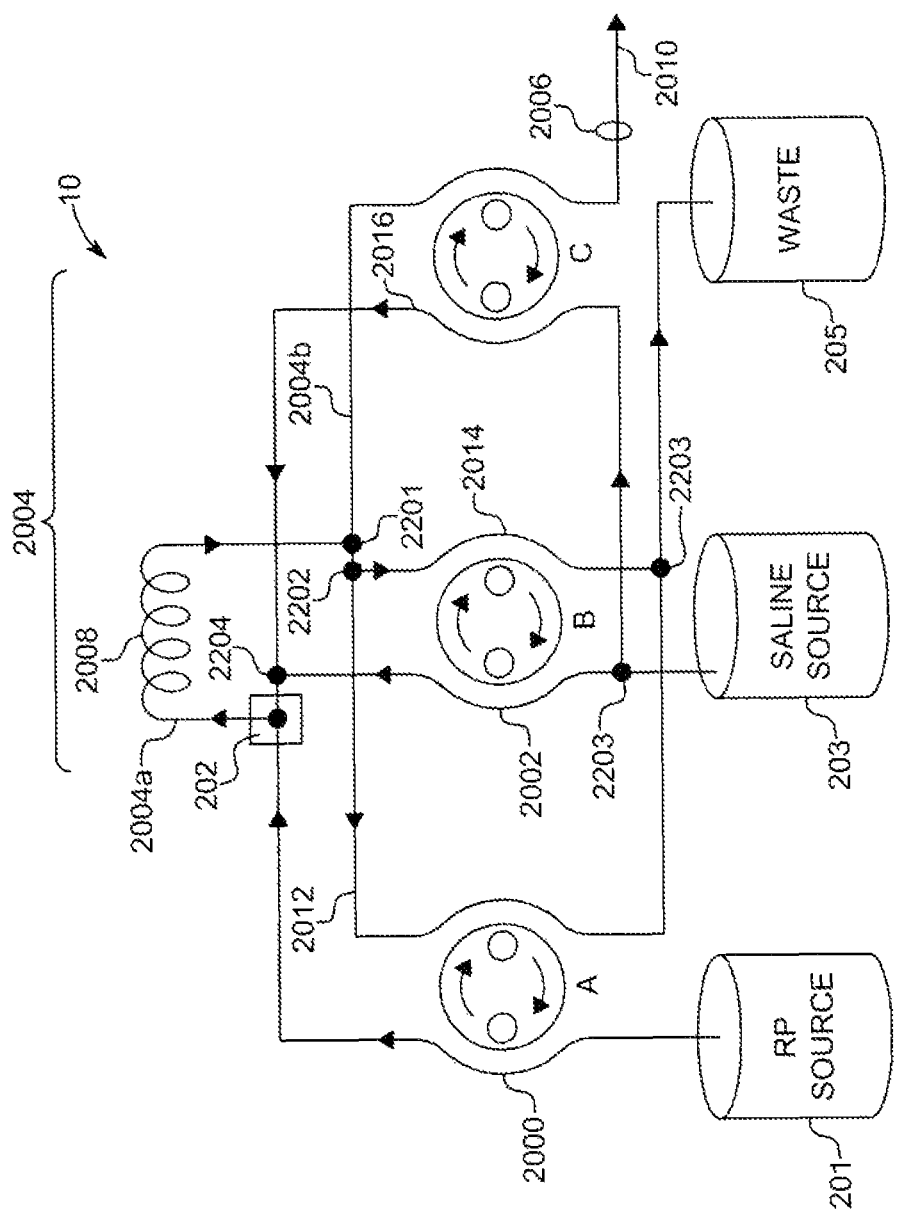
FIG. 1 is a schematic drawing showing one embodiment of the fluid path set and devices contacting the fluid path set of the radiopharmaceutical delivery system of some exemplary embodiments.

The above summary of the present invention is not intended to describe each illustrated embodiment or every possible implementation of the present invention. The detailed description, which follows, particularly exemplifies these embodiments.

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

For purposes of the description hereinafter, the terms "upper," "lower," "right," "left," "vertical," "horizontal," "top," "bottom," "lateral," "longitudinal," and derivatives thereof shall relate to the orientation of embodiments disclosed in the drawing figures. However, it is to be understood that embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

It is to be understood that the disclosed embodiments may assume various alternative variations and step sequences, except where expressly specified to the contrary. It is also to be understood that the specific devices and processes illustrated in the attached drawings, and described in the following specification, are simply exemplary embodiments.

As used herein, the term "fluid path set" refers to a one or more sections of tubing designed and configured to fluidly connect elements of the fluid delivery system 10 including a medical fluid source, a radiopharmaceutical source, a pharmaceutical source, and the like to a fluid delivery tube configured arranged to deliver medical fluid and the radiopharmaceutical and/or the pharmaceutical to a patient. In various embodiments, the one or more sections of tubing making up the fluid path set may be joined to one another in a manner that allows fluids traveling within the tubing to be carried to various portions of the system, mixed with one another, delivered to a patient or a waste receptacle. Thus, the fluid path set may include one or more joints including, but not limited to, linear joints, T-joints, 4-way joints, and the like. In still other embodiments, the one or more of the one or more joints may include valves such as, for example, check valves, by-pass valves, stop cocks, and the like, and combinations thereof. The fluid path set of various embodiments may further include one or more fittings that link the fluid path set or portions thereof to the medical fluid, radiopharmaceutical, pharmaceutical, and patient. Such fittings may include Luer fittings, screw-type fittings, pressure fittings, and the like and combinations thereof.

In some embodiments, tube set may include a delivery tube section, that is used on a per-patient basis and discarded after use with a single patient to prevent, for example, cross-contamination between patients that can be collectively be referred to as "single patient delivery set" ("SPDS") or "patient administration set" ("PAS"). The remaining portions of the fluid path set in which the radiopharmaceutical is calibrated and prepared for delivery can be used for multiple patients and can be referred to as a "multiple patient delivery set" ("MPDS") or "source administration set" ("SAS").

In certain embodiments, the MPDS may include no controllable valves, and in particular, no pinch valves. An exemplary fluid path set is illustrated in the schematic of FIG. 1. In the fluid path set of FIG. 1, fluid flow is controlled by the action of three roller pumps (A, B, C). Each roller pump simultaneously contacts two separate portions of the fluid path set and maintains fluid flow of two segments of the fluid path set. In some embodiments, each roller pump A, B, C, may operate unidirectionally, i.e., rotate only in one direction. In other embodiments, one or more of the roller pumps may be capable of rotating in both a forward and reverse direction, and in still other embodiments, all of the roller pumps may be capable of operating in forward and reverse directions. With regard to the schematic of FIG. 1, each roller pump is unidirectional, rotating in the directions identified by the arrows.

The fluid path set may include any number of tubing segments. For example, as illustrated in FIG. 1, a first tubing section 2000 may fluidly connect a pharmaceutical source 201 to a confluence 202. The flow of fluid in the first tubing section 2000 may be regulated and controlled by action of roller pump A, such that when roller pump A is activated fluid may flow from the pharmaceutical source 201 to the confluence 202 through the first tubing section 2000. When roller pump A is not activated, no fluid flows from the pharmaceutical source 201 and no pharmaceutical enters the fluid path set. A second tubing section 2002 may fluidly connect a source of medical fluid 203 to the confluence 202, and the flow of fluid through the second tubing section 2002 may be controlled by action of roller pump B, such that activation of roller pump B causes fluid from the medical fluid source 203 to flow through the second tubing section 2002 to the confluence 202. In some embodiments, a third tubing section 2004 may be fluidly connected to the confluence 202 and an exit port 2006. The exit port 2006 may be designed and configured to attach to an SPDS 2010 for delivery of the fluid to a patient.

In certain embodiments, the fluid delivery system may be designed to deliver a radiopharmaceutical and may incorporate devices for measuring the activity of a dose of radiopharmaceutical and providing a prescribed dose of radiopharmaceutical accurately. For example, in some embodiments, the third tubing section 2004 may include a first portion of the third tubing section 2004a and a second portion of the third tubing section 2004b, and a measurement coil 2008 may be disposed between the first portion of the third tubing section 2004a and the second portion of the third tubing section 2004b. In some embodiments, the measurement coil 2008 may be incorporated directly into the third tubing section 2004 such that the first portion of the third tubing section 2004a, the measurement coil 2008, and the second portion of the third tubing section 2004b are formed from a continuous unbroken length of tubing. In other embodiments, the measurement coil 2008 may be a separate section of tubing that is connected to the first portion of the third tubing section 2004a and the second portion of the third tubing section 2004b by fittings such as, for example, Luer, screw, snap, or pressure fittings. The measurement coil 2008 will generally have a predetermined length and volume and may be designed to fit within an activity measuring device associated with the fluid delivery device. In operation, the activity level of the radiopharmaceutical can be determined while the radiopharmaceutical is carried through measurement coil 2008 in the ion chamber before being delivered to the exit port 2006 and ultimately administered to the patient.

The fluid path set may include any number of additional tubing sections that can be arranged to facilitate movement and transport of the medical fluid and pharmaceutical through the system, flushing of the system, and the like. For example, in some embodiments, the fluid path set may include a fourth tubing section 2012 that fluidly connects the third tubing section 2004 or a portion thereof to a waste receptacle 205. In such embodiments, a T-joint 2201 may connect the third tubing section 2004 to the fourth tubing section 2012. The T-joint 2201 may be configured to allow free flow of fluid through the second portion of the third tubing section 2004b to the exit port 2006 and from the second portion of the third tubing section 2004b to the fourth tubing section 2012. Movement of fluid through the T-joint 2201 can be regulated based on selective activation of the roller pumps. For example, in the fluid path illustrated in FIG. 1, movement of fluid toward the exit port 2004b through the second portion of the third tubing section 2004b can be achieved by inactivating of roller pump A stopping fluid flow through the fourth tubing section 2012 and activating roller pump C, which draws fluid through the second portion of the third tubing section 2004b toward the exit port 2006. Because fluid flow is stopped in the fourth tubing section, fluid must flow to the right (as drawn) at the T-joint 2201. Conversely, inactivating roller pump C stopping fluid flow through the second portion of the third tubing 2004b section and activating roller pump A causes fluid to flow through the fourth tubing section 2012 to the waste receptacle 205.

The fluid path set may further include one or more by-pass tubing sections that allow for fluid flow by-passing particular roller pumps. For example, as illustrated in FIG. 1, in some embodiments, a waste by-pass tubing section 2014 may connect an upstream portion of the fourth tubing section 2012 through a T-joint 2202 with a downstream portion of the fourth tubing section 2012 through a T-joint 2203. As depicted, fluid flow through the waste by-pass tubing section 2014 may be initiated by activation of roller pump B allowing fluid to flow to the waste receptacle 205 even when roller pump A is inactive. This arrangement allows medical fluid from the fluid source 203 to flow through the second tubing section 2002, confluence 202, third tubing section 2004, and in certain embodiments, the measurement coil 2008 and into the waste receptacle 205 through the waste by-pass tubing section 2014 when roller pump B is activated and roller pumps A and C are inactive. This allows these tubing sections to be primed, such that air in the fluid path set can be replaced with fluid.

In certain embodiments, the fluid path set may include a medical fluid by-pass tubing section 2016 connecting an upstream portion of the second tubing section 2002 at a T-joint 2203 to a downstream portion of the second tubing section 2002. In some embodiments, as illustrated in FIG. 1, a T-joint 2204 may connect the downstream portion of the second tubing section 2002 to the medical fluid by-pass tubing section 2016. In other embodiments, the medical fluid by-pass tubing section 2016 may connect directly to the confluence 202 thereby by-passing the second tubing section 2002 completely. In operation, the inactivating roller pump B and activating roller pump C will allow fluid to flow from the medical fluid source 203 to the confluence 202, into the third tubing section 2004 to the exit port 2006 and to the patient through the SPDS 2010.

The tubing set illustrated in FIG. 1 may include any number of additional tubing sections, by-pass sections, T-joints, confluences, and the like, and in particular embodiments, the fluid set path may include check valves or other means for reducing or eliminating backflow of fluid. Such check valves can be introduced on any tubing section at any position along the tubing sections where backflow may be problematic. In certain embodiments, a first check valve associated with the confluence 202 may be located in or near the confluence 202 to eliminate back flow into the first tubing section 2000, and a second check valve associated with the confluence 202 may be located in or near the confluence 202 to eliminate backflow into the second tubing section 2002. These check valves may reduce the likelihood of contamination of the medical fluid source 203 with pharmaceutical and reduce the likelihood of dilution of the pharmaceutical source 201 with medical fluid. Additional check valves may be located near T-joints and by-pass tubing sections to reduce contamination when, for example, fluids are shunted to the waste receptacle 205.

While some embodiments described herein include specific mention of a measurement coil 2008 for measuring the radioactive emissions of a radiopharmaceutical, other embodiments are not limited to measurement coils for measuring radioactive emissions. For example, in some embodiments, the pharmaceutical may be measured by volume alone, and thus, no measurement coil may be necessary. In other embodiments, the measurement coil 2008 may be configured and arranged for analyte detection allowing the amount of a particular analyte to be measured before delivery to a patient.

In some embodiments, the confluence 202 may be configured to accept fluids from more than two sources. For example, in some embodiments, confluence may be configured to accept fluid from 3, 4, 5, or 6 sources. In such embodiments, additional tubing sections may be configured to carry the additional fluids from a source to the confluence. In some embodiments, the roller pumps (A, B, C) described above may control flow of the additional fluids by, for example, replacing a by-pass tubing section with a tubing section for introducing an additional fluid from a source to the confluence. In other embodiments, additional roller pumps may be used to control the flow of the additional fluids, and in certain embodiments, other types of pumps may be used to control the flow of additional fluids. For example, a manual or stepper motor driven syringe may be used to introduce certain fluids into the confluence or a peristaltic pump or other in-line pump may be used to introduce a fluid into the confluence. In some embodiments, a check valve may be incorporated into the confluence to allow for one-way fluid flow of the additional fluid and reduce back flow or contamination.

In some embodiments, the tube set described herein may include one or more additional confluences for introducing additional fluids into a tubing section. For example, in certain embodiments a second confluence may be positioned in the second portion of the third tubing section 2004b that allows for the addition of another fluid before the fluid is delivered to the patient. The additional fluid can be added before, during, or after administration of the radiopharmaceutical, without interrupting the flow of medical fluid to the patient. For example, in certain embodiments, a syringe or vial including a pharmaceutical agent such as a stimulant may be introduced into the flow path through a second confluence in the second portion of the third tubing section 2004b. In other embodiments, a pharmaceutical delivery port may be provided in a portion of the delivery tubing section or SPDS, and may be configured to allow introduction of a pharmaceutical agent into the delivery tubing section or SPDS during a procedure. In such embodiments, the pharmaceutical delivery port may be any type of port known in the art such as, but not limited to, a Luer, a needle vial adaptor, needleless vial adaptor, or other fitting capable of accepting a delivery device such as a syringe or vial and allowing access to fluid flow in the fluid path set. In still other embodiments, fluid may be diverted into the syringe or vial where the pharmaceutical is mixed with the fluid before being introduced back into the fluid path set before the delivery tube section or SPDS. The systems of such embodiments may include one or more pumps, motors, or the like associated with the second confluence, pharmaceutical delivery port, or delivery tube section or SPDS. In some embodiments, the pharmaceutical delivery port may be absent, blocked, or otherwise eliminated such that the radiopharmaceutical can be delivered in the absence of the addition of an additional pharmaceutical or stimulating agent.

Each component of the fluid path sets described herein may be pre-connected and can be stored in a sterile packet or container for use in a fluid delivery system. In various embodiments, the first tubing section 2000 may include a connector such as a spike or vented cannula for connecting the first tubing section to the pharmaceutical or radiopharmaceutical vial 201, and the second tubing section may include a spike or Luer lock for connecting to the medical fluid storage device 203. Further connectors may be associated with the coil assembly 2008 and waste receptacle 205. In certain embodiments, a connector may be associated with the exit port 2006 to connect the third tubing section 2004 to a SPDS, and one or more valves may be associated with such connectors. In some embodiments, the connector at the exit port 2006 may be a swabable valve that can be disinfected or washed when the SPDS is replaced between patients. In some embodiments, the SPDS connector can be encoded through RFID, light sensors, mechanical sensors, etc. to ensure that the correct SPDS is connected. This ensures that the correct protocol is executed with the correct SPDS.

Figure 2:
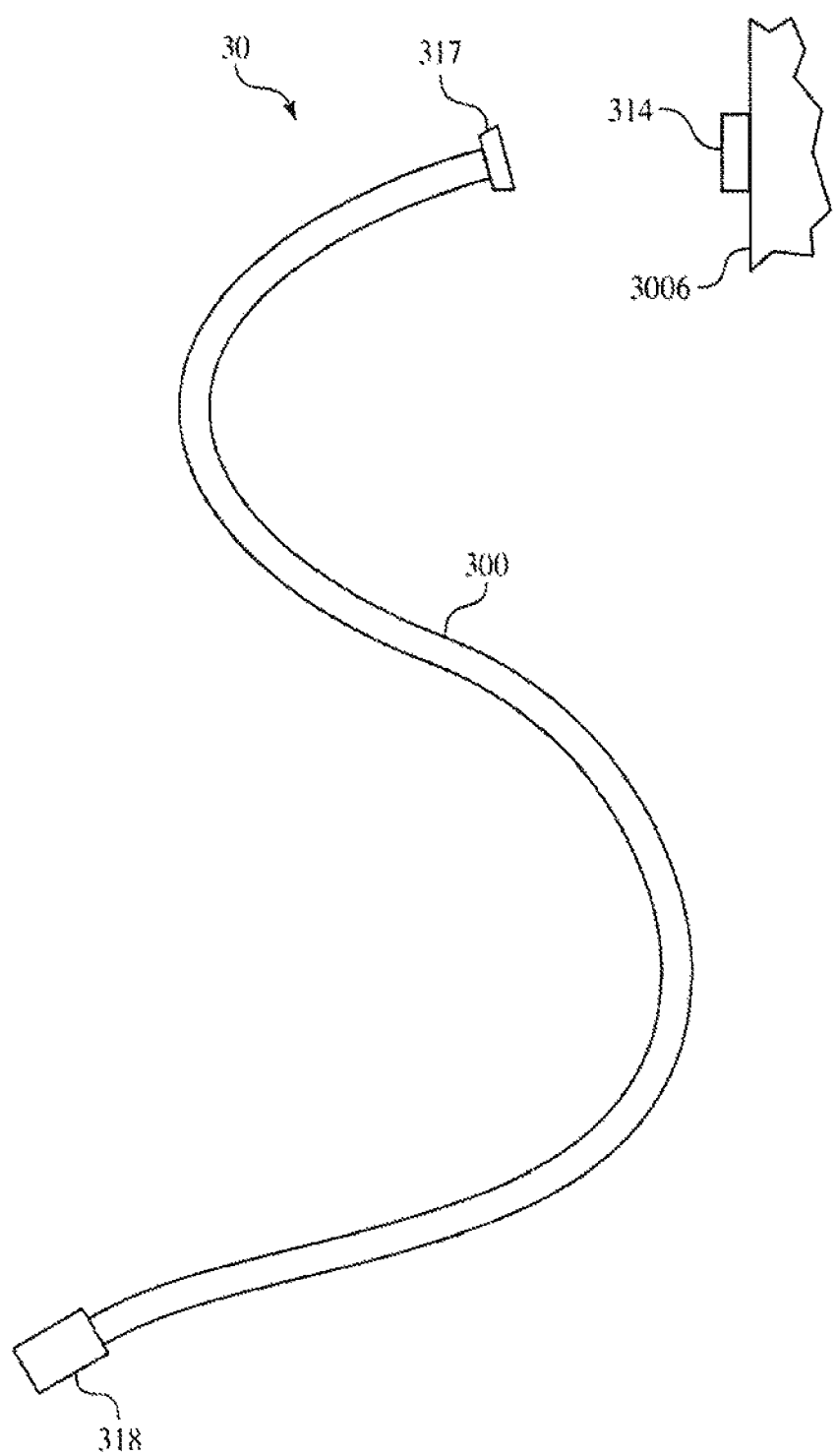
FIG. 2 is a drawing of a single patient delivery system.

In various embodiments as illustrated in FIG. 2, the delivery tube section or SPDS 30 may include a length of tubing 300 having a proximal fitting 317 that can be reversibly attached to the connector 314 associated with the exit port 3006 of a delivery device. In some embodiments, the delivery tube section or SPDS 30 may have a proximal fitting 317 that can be reversibly attached to a T-joint or valve associated with a pharmaceutical delivery port. A distal fitting 318 having a connector capable of being attached to, for example, a catheter, IV needle, intravenous port, or the like such as, for example, a Luer connector, can be included at the distal end of the length of tubing 300 and may provide a means for delivery of the radiopharmaceutical to a patient. The distal fitting 318 may be configured to connect to typical patient delivery apparatuses such as, IV needles, ports, catheters, or other means for delivering intravenous pharmaceuticals. In other embodiments, the delivery tube section or SPDS 30 may incorporate such delivery devices, and in still other embodiments, the delivery tube section or SPDS 30 may be configured to connect to other sections of tubing, which may incorporate the delivery apparatuses.

The systems of various embodiments may be configured to deliver any radiopharmaceutical known in the art, and the radiopharmaceutical may be delivered alone or in combination with another pharmaceutical composition. For example, in some embodiments, the system may be designed and configured to deliver $^{47}$Ca—Ca$^{2+}$, $^{11}$C-L-methyl-methionine, $^{14}$C-glycocholic acid, $^{14}$C-para-amino benzoic acid (PABA), $^{14}$C-urea, $^{14}$C-d-xylose, $^{51}$Cr-red blood cells, $^{51}$Cr—Cr$^{3+}$, $^{51}$Cr-ethylenediaminetetraacetic acid (EDTA), $^{57}$Co-cyanocobalamin (vitamin B$_{12}$), $^{58}$Co-cyanocobalamin (vitamin B$_{12}$), $^{169}$Er-colloid, $^{18}$F-fluorodeoxyglucose (FDG), $^{18}$F-fluoride, $^{18}$F-fluorocholine, $^{68}$Ga-dotatoc or dotatate, $^{3}$H-water, $^{111}$In-diethylenetriaminepenta-acetic acid (DTPA), $^{111}$In-leukocytes, $^{111}$In-platelets, $^{111}$In-pentetreotide, $^{111}$In-octreotide, $^{123}$I-iodide, $^{123}$I-o-iodohippurate, $^{123}$I-m-iodobenzylguanidine (MIBG), $^{123}$I-FP-CIT, $^{125}$I-fibrinogen, $^{131}$I-iodide, $^{131}$I-m-iodobenzylguanidine (MIBG), $^{59}$Fe—Fe$^{2+}$ or Fe$^{3+}$, $^{81m}$Kr-aqueous, $^{13}$N-ammonia, $^{15}$O-water, $^{32}$P-phosphate, $^{82}$Rb-chloride, $^{153}$Sm-ethylenediaminotetramethylenephosphoric acid (EDTMP), $^{75}$Se-selenorcholesterol, $^{75}$Se-23-Seleno-25-homo-tauro-cholate (SeHCAT), $^{22}$Na—Na$^{+}$, $^{24}$Na—Na$^{+}$, $^{89}$Sr-chloride, $^{99m}$Tc-pertechnetate, $^{99m}$Tc-human albumin, $^{99m}$Tc-human albumin macroaggregates or microspheres, $^{99m}$Tc-phosphonates and phosphate, $^{99m}$Tc-diethylenetriaminepenta-acetic acid (DTPA), $^{99m}$Tc-dimercaptosuccinic acid (V) (DMSA), $^{99m}$Tc-dimercaptosuccinic acid (III) (DMSA), $^{99m}$Tc-colloid, $^{99m}$Tc-hepatic iminodiacetic acid (HIDA), $^{99m}$Tc-denatured red blood cells, $^{99m}$Tc-red blood cells, $^{99m}$Tc-mercaptoacetyltriglycine (MAG3), $^{99m}$Tc-exametazime, $^{99m}$Tc-sestamibi (MIBI-methoxy isobutyl isonitrile), $^{99m}$Tc-sulesomab (IMMU-MN3 murine Fab'-SH antigranulocyte monoclonal antibody fragments), $^{99m}$Tc-human immunoglobulin, $^{99m}$Tc-tetrofosmin, $^{99m}$Tc-ethyl cysteinate dimer (ECD), $^{201}$Tl—Tl$^{+}$, $^{133}$Xe in isotonic sodium chloride solution, $^{90}$Y-silicate, and the like and combinations thereof. In certain embodiments, the system may be configured for delivery of radiopharmaceuticals for imaging myocardial or other cardiovascular conditions during, for example, a stress test. In such embodiments, the system may be configured to deliver $^{18}$F-fluorodeoxyglucose (FDG), $^{13}$N-ammonia, $^{15}$O-Water, $^{82}$Rb-Chloride, $^{99m}$Tc-pertechnetate, $^{99m}$Tc-human albumin, $^{99m}$Tc-human albumin macroaggregates or microspheres, $^{99m}$Tc-diethylenetriaminepenta-acetic acid (DTPA), $^{99m}$Tc-denatured red blood cells, $^{99m}$Tc-red blood cells, $^{99m}$Tc-exametazine, $^{99m}$Tc-sestamibi (MIBI-methoxy isobutyl isonitrile), $^{99m}$Tc-tetrofosmin, $^{201}$Tl—Tl$^{+}$, and the like and combinations thereof.

In embodiments in which radiopharmaceuticals are delivered, the fluid path set may include a measurement coil 2008 that positions the radiopharmaceutical to allow for measurement of the emissions by the components surrounding the activity measuring device. More specifically, the measurement coil 2008 orients and locates the radiopharmaceutical within a "linear region" of the activity measuring device to accurately measure its activity level and prepare an optimal dose for injection into a patient. In some embodiments, the measurement coil 2008 may include a section of gathered tubing in a coiled or an uncoiled, amorphous fashion that can be placed inside an activity measuring device associated with the delivery device, or in other embodiments, the measurement coil 2008 may be wound in a specific pattern. The coil assembly may be an individually constructed unit, and in other embodiments, the coil assembly 2008 may include all or portions of third tubing section 2004.

Figure 3A:
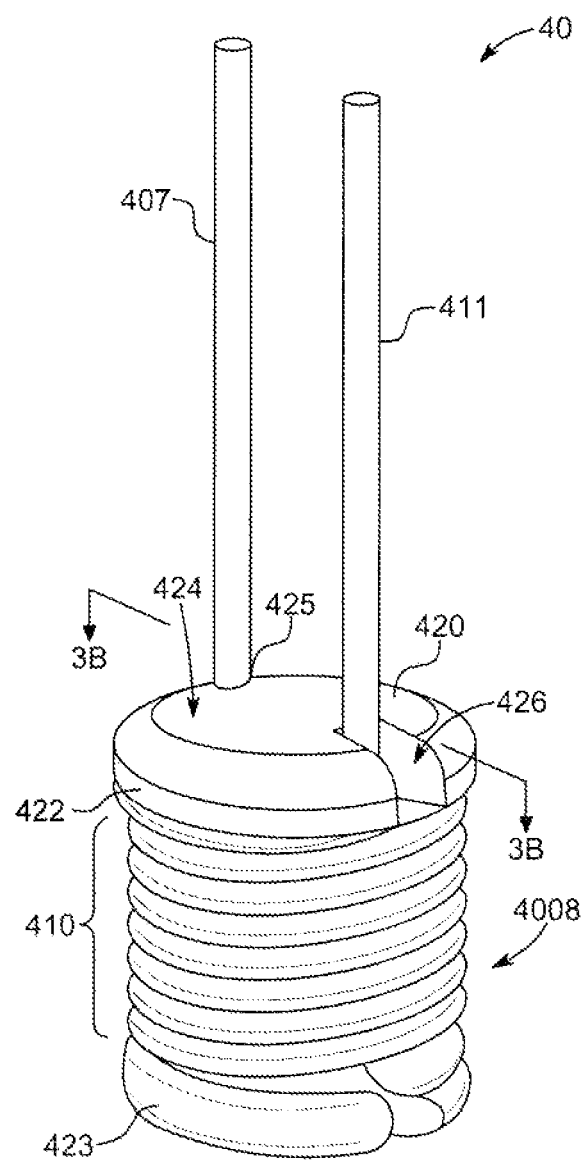
FIG. 3A is a schematic drawing showing external features of the tube coil of the radiopharmaceutical delivery system of some exemplary embodiments.
Figure 3B:
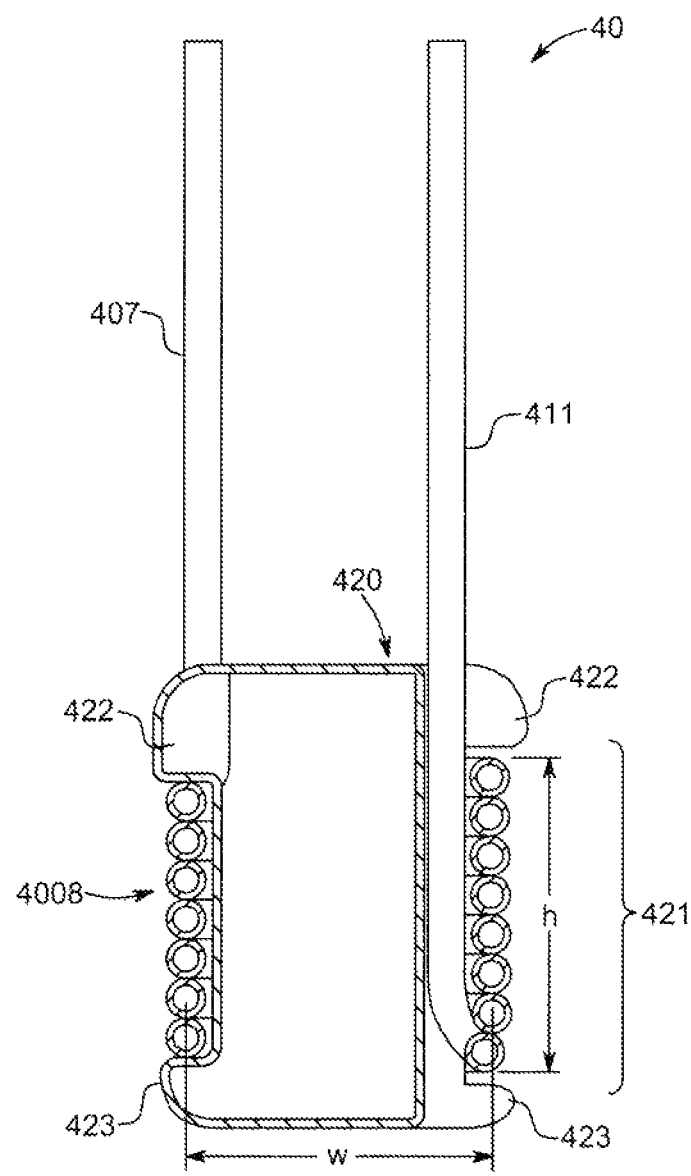
FIG. 3B is a schematic drawing showing a cross-section of the tube coil of the radiopharmaceutical delivery system of some exemplary embodiments.

In certain embodiments, the measurement coil 2008 may include a length of tubing that is coiled on itself or stacked in a coil. The tubing layers may be bonded together to maintain this configuration, and in some embodiments, as illustrated in FIG. 3A and 3B, the measurement coil 4008 may include a core element or structure 420 onto which a tube coil 410 is wrapped. The core element 420 may be configured to facilitate optimal positioning of the tube coil 410, and may be sized to fit within the activity measuring device in the delivery device. In some embodiments, the core element 420 may include a tube channel 421 between an upper shoulder 422 and a lower shoulder 423. The tube coil 410 may be retained within the tube channel 421 and between the upper and lower shoulders 422, 423 to hold the tube coil 410 in position and prevent kinking. In further embodiments, an upper surface 424 of core element 420 may include one or more inlet channels or grooves 425 and an outlet channel or groove 426 to accommodate inlet third tubing section 407 and fourth outlet third tubing section 411, respectively.

In various embodiments, the coil assembly 40 may be positioned concentrically in the activity measuring device, and the core element 420 may be self-centering when inserted into the activity measuring device of the fluid delivery system to facilitate optimal positioning and performance. This may be achieved either through structural features of the measurement coil 4008, the structure of core element 420, or a combination thereof. For example, in some embodiments, the upper shoulder 422, the lower shoulder 423, or both can be configured to associate with an outer wall of the activity measuring device. The core element 420 may include additional features such as, for example, extensions, indentations, or notches may be provided on the core element 420 either on the upper or lower shoulders 422, 423 or another portion of the coil assembly 40, that engage corresponding elements in the activity measuring device to aid in the proper positioning of the measurement coil 4008. In other embodiments, the lower shoulder 423 may be sized to provide an appropriate distance between the lower surface of the activity measuring device when the lower shoulder contacts the lower surface of the activity measuring device or a diameter that corresponds with a the appropriate diameter of the activity measuring device.

With reference to FIG. 3B, in particular embodiments, the core element 420 and the tube coil 410 may be sized and dimensioned so that the measurement coil 4008 can be optimally positioned within the "linear region" of the activity measuring device The "linear region" of an activity measuring device refers to the region of the chamber in which activity level measurements are repeatable and predictable. For an exemplary activity measuring device (Model IK-102 Short Activity measuring device provided by Veenstra Instruments), the "linear region" is located within a window of about 5 mm to about 65 mm measured from the base or bottom wall of the activity measuring device. The measurement coil 4008 of various embodiments may have a volume capacity of about 1 ml to about 10 ml or about 1.5 ml to about 7 ml and may be configured in any way to achieve the desired volume. Moreover, the tube coil 410 may have any number of turns. For example, in some embodiments, the measurement coil 4008 may have about 4 to about 10 turns, and in other embodiments, the measurement coil 4008 may have about 5 to about 7 turns. In various embodiments, the measurement coil 4008 may have one or more ½ or ¼ turns that allow appropriate placement of the inlet tube section 407 and outlet tube section 411. A tube coil having this number of turns may be formed from any length of tubing sufficient to make the desired number of turns based on the diameter of the core element 420. For example, a core element 420 having a diameter (w) of about 0.5 in to about 4 in or about 1 in to about 3 may require tubing having a length of about 5 in to about 24in, about 8 in to about 15 in, or about 10 in to about 12 in. The height (h) of the tube coil 410 may similarly vary depending on the number of turns, the diameter of the tubing, and the diameter to the core element. For example, a measurement coil 4008 having from about 5 to about 7 turns may have a height (h) of from about 0.5 in to about 8 in or about 1 in to about 5 in. The measurement coil 4008 may be prepared from any type of tubing; however, in certain embodiment, the tubing may have an OD of from about 0.01 in to about 0.5 in and an ID of about 0.025 to about 0.5 in.

In some embodiments, the system 10 may include one or more additional components including, but are not limited to, air detectors, mounts or retainers for holding the connector ends of the delivery tube section, and the like and combinations thereof.

The tubing of each of the sections of the fluid path sets described above, i.e., MPDS and SPDS, may be prepared from the same or different materials. For example, in various embodiments, the tubing may be silicone, C-Flex, standard PVC, silicone-like PVC material, or pump tubing. In particular embodiments, the microbore tubing may be formed from, for example, silicone, C-Flex, or silicone-like PVC material, and the other tubing sections may be formed from any suitable polymeric material, including standard PVC. In some embodiments, the tubing may be a coextruded or multilayered tubing having two or more layers of materials. For example, in various embodiments, the tubing may have an inner layer of a first material such as those identified above, and an outer layer of a second material that is different from the first material. In certain embodiments, a third layer may be disposed between the inner and outer layers. Such multi-layer tubing is known in the art and commercially available.

The dimensions of the components of the fluid path sets described above, Including the various tubing sections, may vary among embodiments and may depend, for example, on the procedure for which the system is being used and the type and amount of radiopharmaceutical being delivered. In certain exemplary embodiments, the first, second, third, and by-pass tubing sections may have an outer diameter (OD) of about 0.05 inches to about 0.25 inches or about 0.17 inches and an inner diameter (ID) of about 0.05 inches to about 0.15 inches or about 0.08 inches, and may have a hardness of about 90 to about 95 Shore A durometer. In some embodiments, the first tubing section 2000 can be formed of microbore tubing having an OD of about 0.05 inches to about 0.10 inches or about 0.09 inches, an ID of about 0.01 inches to about 0.07 inches or about 0.03 inches and a hardness of about 35 to about 55 or about 45 Shore A durometer. The use of microbore tubing in first tubing section 2000 can improve volume accuracy and thereby improves measured activity accuracy (i.e., of pharmaceutical delivered to the patient) and reduces pharmaceutical waste. All of these dimensions are provided for exemplary purposes only and are not to be construed as limiting this disclosure.

In various embodiments, pharmaceutical source 201 may be a multi-dose container configuration to hold and store a sufficient amount of pharmaceutical for delivery to multiple patients in a single container. In other embodiments, pharmaceutical source may be more than one container or vial of the pharmaceutical, and the containers or vials may be contained in a well configured to hold more than one container or vial. In some embodiments, each container in the multi-container configuration may include individual doses of pharmaceutical sufficient for administration to a single patient. In other embodiments, each container or vial may hold and store multiple doses of the pharmaceutical and the system may be configured such that doses of the pharmaceutical can be pulled from a new vial when the proceeding vial is used to completion. In still other embodiments, different pharmaceutical compositions may be held and stored in each of two or more different multi-dose containers, and the system may be configured to deliver different pharmaceutical compositions either simultaneously or consecutively to the same or different patients.

In embodiments in which the fluid path set described herein is used for delivery of a radiopharmaceutical, the radiopharmaceutical source 201 may be any suitable radiopharmaceutical container or vial known in the art, and the device associated with the fluid path set may include a well for holding the radiopharmaceutical that is configured to accept such container or vial and securely hold the container during use. In some embodiments, an adaptor may be used that encases all or a portion of the vial or container before it is placed in the well to ensure that the vial or container is secured. In such embodiments, the container, vial, well, adaptor, or any combination thereof may be prepared from or include a material that blocks emission of the radioactive particles from the radiopharmaceutical.

Embodiments are not limited to a particular pharmaceutical agent, and any agent that is known or may be usefully administered may be contained within the syringe and administered to the patient during a procedure. For example, in some embodiments, the pharmaceutical agent may be a stress agent such as, but not limited to, IV Dobutamine, IV Dipyridiamole (Persantine), IV Adenosine (Adenoscan), IV Lexiscan (Regadenoson), and the like. In other embodiments, the pharmaceutical agent may reduce vasodilation such as, for example, IV Aminophylline. In still other embodiments, the system may include a first pharmaceutical delivery port and a second pharmaceutical delivery port. In such embodiments, a first syringe associated with the first pharmaceutical delivery port that holds a stress agent and a second syringe associated with the second pharmaceutical deliver port may include a pharmaceutical that acts to reduce vasodilation and act as an antidote to stress agent, allowing the user to reduce the stress under which the patient is placed as part of the procedure or as a precaution in the event of an adverse event. The pharmaceutical agent can be introduced into the fluid flow through the pharmaceutical delivery port continuously or in one or more controlled doses.

The roller pumps A, B, C, described above with regard to the fluid path sets may be any type of roller pump known in the art, and in some embodiments, these roller pumps may be replaced with other pumping mechanisms. Any suitable type of pumping mechanism can be used including, but not limited to, piston-driven syringe pumps, gear pumps, rotary pumps, in-line pumps, diaphragm, centrifugal pumps, and peristaltic pumps can be used in place of the roller pumps described herein. In further embodiments, a combination of pumps may be used in the same device to control the flow of fluid through fluid path sets such as those described above, and in still other embodiments, roller, gear, diaphragm, centrifugal, or the like pumps may be used in addition to roller pumps A, B, and C to augment or further regulate fluid flow. In various embodiments, the pumping mechanism may be opened to receive a length of tubing associated with the fluid path set.

The pumps of various embodiments may generally be configured to operate independently. Therefore, a user or an operating system can control each pump individually. The pumps can be calibrated to deliver a fluid at a particular flow rate, and in some embodiments, the flow rate can be modified or altered during use. For example, in some embodiments, one rotation of roller pump a may introduce 1 milliliter of fluid into the fluid path set, and 0 5 milliliters of fluid may be introduced into the fluid path set by causing the roller pump to rotate by ½ revolution. Independent operability may also allow the roller pumps to prime various portions of the fluid path set independently, such that air is completely eliminated from the fluid path set before delivery of any fluid to a patient.

Figure 4:
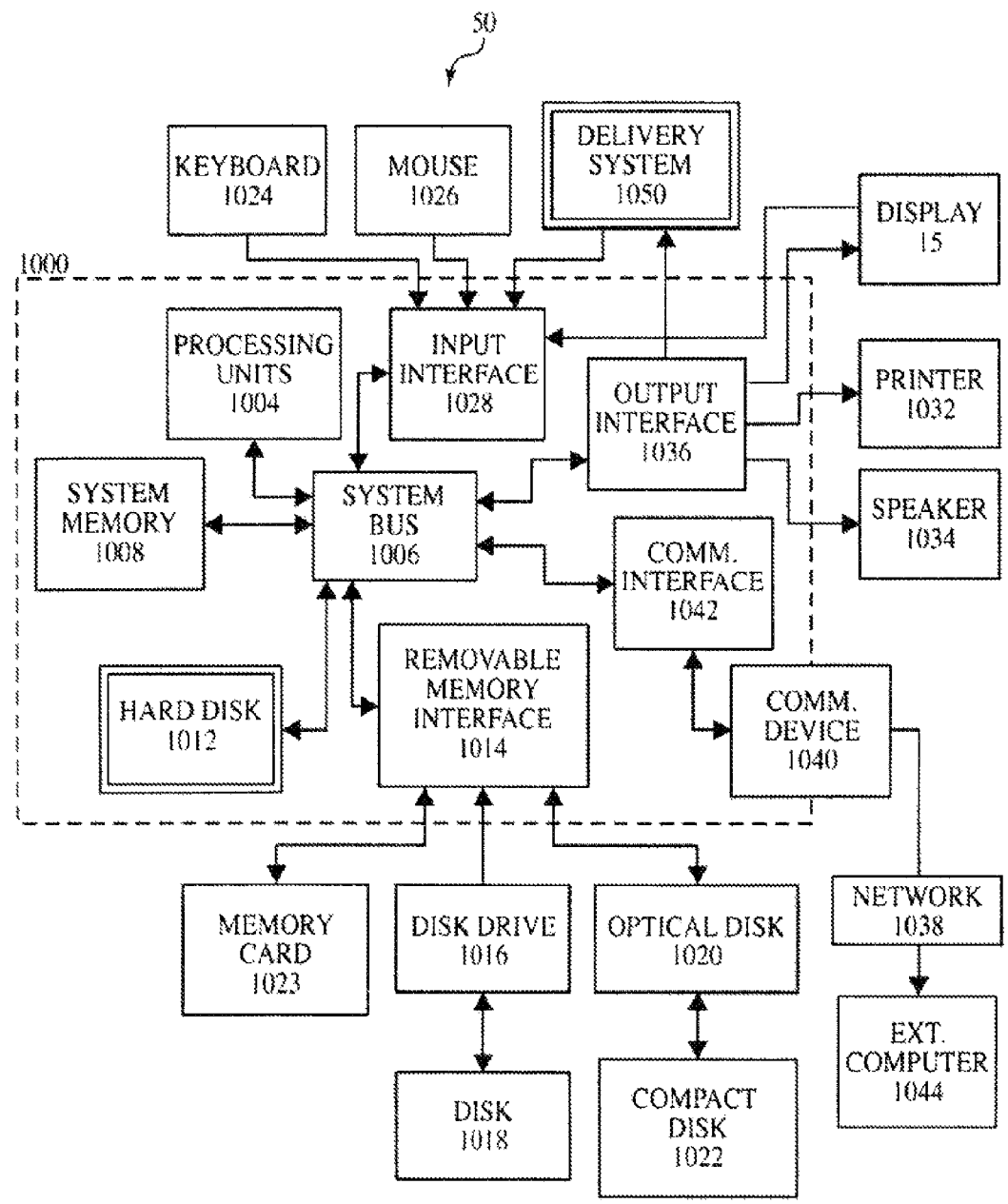
FIG. 4 is a schematic representing the control system of the radiopharmaceutical delivery system of some exemplary embodiments.

In various embodiments, the fluid delivery system may include a control system 50 (schematically represented in FIG. 4) in communication with the various components of the delivery system 1050 that for the purposes of the schematic of FIG. 4 can, include, for example, pumps, motors, activity measuring device, interrupt button, air detectors valves, stopcocks, and the like. The control system 50 may, generally, control the operation of the delivery system 1050, while also providing an interface with input and output devices such as the display 15, printer 1032, and network devices 1038 used to program and direct the action of the delivery system 1050.

The control system 50 may include, but is not limited to, at least one computer 1000 having certain components for appropriate operation, execution of code, and creation and communication of data. The computer 1000 includes one or more processing units 1004 (typically referred to as a central processing unit or CPU) that serves to execute computer-based instructions received in the appropriate data form and format. Further, this processing unit 1004 may be in the form of multiple processors executing code in series, in parallel, or in any other manner for appropriate implementation of the computer-based instructions. As used herein, the computer 1000 may be operably configured to execute appropriate software to perform and implement the processing steps of the methods and systems disclosed herein. The system may include one or more computers 1000 or similar computing devices having a computer-readable storage medium capable of storing computer-readable program code or instructions that cause the processing unit 1004 to execute, configure, or otherwise implement the methods, processes, and transformational data manipulations discussed herein. Still further, the computer 1000 may be in the form of a personal computer coupled to the fluid delivery system 10, a processor formed integrally with the fluid delivery system 10, a computer provided remotely from the fluid delivery system 10, or any other type of computing device having the necessary processing hardware to appropriately process data to effectively implement the method and system described herein.

The control system 50 may further include a system bus 1006 to facilitate appropriate data communication and processing information between the various components of the computer 1000. The system bus 1006 may be any of several types of bus structures, including a memory bus or memory controller, a peripheral bus, or a local bus using any of a variety of bus architectures. In particular embodiments, the system bus 1006 may facilitate data and information communication between the various components (whether internal or external to the computer 1000) through interfaces.

In some embodiments, the computer 1000 may include one or more discrete computer-readable media components. For example, computer-readable media may include any media that can be accessed by the computer 1000, such as volatile media, non-volatile media, removable media, non-removable media, and the like. In certain embodiments, the computer-readable media may include computer storage media, such as media implemented in any method or technology for storage of information such as computer-readable instructions, data structures, program modules, or other data, including, but not limited to, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer 1000. In some embodiments, the computer-readable media may include communications media, such as computer-readable instructions, data structures, program modules, or other data in a modulated data signal such as a carrier wave or other transport mechanism. In other embodiments, the computer-readable media may include any information delivery media, wired media (such as a wired network and a direct-wired connection), and wireless media (such as acoustic signals, radio frequency signals, optical signals, infrared signals, biometric signals, bar code signals, etc.). Combinations of any of the above are also included within the scope of computer-readable media.

In still other embodiments, the computer 1000 may further include system memory 1008 with computer storage media such as volatile and non-volatile memory, ROM, and/or RAM. A basic input/output system (BIOS) with appropriate computer-based routines assists in transferring information between components within the computer 1000 and can be stored in ROM. The RAM portion of the system memory 1008 typically contains data and program modules that are immediately accessible to or presently being operated on by processing unit 1004, e.g., an operating system, application programming interfaces, application programs, program modules, program data, and other instruction-based computer-readable code.

The computer 1000 may also include other removable or non-removable, volatile or non-volatile computer storage media products. For example, the computer 1000 may include a non-removable memory interface 1010 that communicates with and controls a hard disk drive 1012, i.e., a non-removable, non-volatile magnetic medium, a removable, non-volatile memory interface 1014 that communicates with and controls a magnetic disk drive unit 1016 (which reads from and writes to a removable, non-volatile magnetic disk 1018), an optical disk drive unit 1020 (which reads from and writes to a removable, non-volatile optical disk, such as a CD ROM 1022), a Universal Serial Bus (USB) port for use in connection with, for example, a removable memory card 1023. Other removable or non-removable, volatile or non-volatile computer storage media can be used in the exemplary computing system environment, including, but not limited to, magnetic tape cassettes, DVDs, digital video tape, solid state RAM, solid state ROM, and the like. These removable or non-removable, volatile or non-volatile magnetic media are in communication with the processing unit 1004 and other components of the computer 1000 via the system bus 1006. The drives and their associated computer storage media discussed above and illustrated in FIG. 4 provide storage of operating systems, computer-readable instructions, application programs, data structures, program modules, program data, and other instruction-based computer-readable code for the computer 1000 (whether duplicative or not of the information and data in the system memory 1008).

In particular embodiments, the fluid delivery system may be configured to allow a user to enter commands, information, and data into the computer 1000 using the touch-screen of the GUI display 15 via an operator input interface 1028. However, it has been envisioned that an operator may enter commands, information, and data into the computer 1000 using other attachable or operable input devices, such as a keyboard 1024, a mouse 1026, a remote control device, a microphone, a trackball, a joystick, a touchpad, a scanner, a tablet computer, and the like, via the operator input interface 1028. Any arrangement that facilitates the input of data and information to the computer 1000 from an outside source may be used including, for example, hard wiring or accessing using a wireless network device, such as blue tooth, a wireless internet connection, or a cellular connection. As discussed, these and other input devices are often connected to the processing unit 1004 through the operator input interface 1028 coupled to the system bus 1006, but may be connected by other interface and bus structures, such as a parallel port, game port, or a USB.

In still further embodiments, data and information can be presented or provided to an operator in an intelligible form or format through certain output devices, such as the GUI display 15 (to visually display this information and data in electronic form), a printer 1032 (to physically display this information and data in print form), a speaker 1034 (to audibly present this information and data in audible form), etc. All of these devices are in communication with the computer 1000 through an output interface 1036 coupled to the system bus 1006.

The computer 1000 may operate in a network environment 1038 through the use of a communications device 1040, which is integral to the computer or remote. This communications device 1040 is operable by and in communication with the other components of the computer 1000 through a communications interface 1042. Using such an arrangement, the computer 1000 may connect with or otherwise communicate with one or more remote computers, such as a remote computer 1044 of a hospital information system, which typically includes many or all of the components described above in connection with the computer 1000. Using appropriate communications devices 1040 such as, for example, a modem, a network interface, adapter, telephone line, cellular telephone connection, wifi network, and the like, the computer 1000 may operate within and communicate through a local area network (LAN) and a wide area network (WAN), but may also include other networks such as a virtual private network (VPN), an office network, an enterprise network, an intranet, the Internet, and the like and combinations thereof. It will be appreciated that the network connections shown are exemplary and other means of establishing a communications link between the computers 1000, 1044 may be used.

The system may be further configured to provide feedback information to the operator. For example, in some embodiments, the system may provide the operator with information regarding the administration such as, but not limited to, the dosage of radiopharmaceutical delivered to the patient by milligram (mg), volume (ml), and/or radioactive activity (mCi), the amount of other pharmaceutical composition delivered to the patient (mg/ml), the flow rate of the radiopharmaceutical or other pharmaceutical (ml/s), the amount of saline administered (ml), dosing time (i.e., the time required for delivery), the delivery time (i.e., the time of day), date, and the fluid pressure in the delivery system during delivery. In particular embodiments, the system may further provide the operator with absorption data with regard to the particular radiopharmaceutical administered including the expected amount of the radiopharmaceutical absorbed by particular organs such as brain, lung, liver, kidney, bladder, bone, thyroid, heart, breast, stomach, colon, and skin. In some embodiments, the system may reference patient data to determine the amount of radiopharmaceutical administered to the particular patient over time and provide a warning to the operator if absorbed levels become too high. In various embodiments, the information may be provided to the operator in real time or provide an estimate of the absorption, based on the planned dose, prior to an injection.

Following administration or the completion of an administration protocol, the system may provide a summary of the procedure including any relevant data. For example, in various embodiments, the system may provide the dosage of radiopharmaceutical delivered to the patient by milligram (mg), volume (ml), and/or radioactive activity (mCi), the amount of other pharmaceutical composition delivered to the patient (mg/ml), the flow rate of the radiopharmaceutical or other pharmaceutical (ml/s), the amount of saline administered (ml), dosing time (i.e., the time required for delivery), the delivery time (i.e., the time of day), date, and the fluid pressure in the delivery system during delivery and the like and combinations thereof. The system may further provide absorption data such as that described above.

The data provided either in real time during performance of the protocol or in summary of the procedure may be provided numerically or graphically, and in certain embodiments, the screens providing the data may provide both numeric and graphic data simultaneously.

The system may further provide the patients name and any critical data such as, height, weight, allergies, disease being treated or tested for, the procedure to be performed, the location of the injection/infusion site, and the like and various combinations thereof. Such data may be inputted at the time of the procedure or may be inputted prior to the procedure. In certain embodiments, the operator may input the patients name and the system may retrieve appropriate patients data from electronically archived patient records using a computer network or Internet connection. In still further embodiments, the system may store patient information for more than one procedure. For example, in some embodiments, a patient schedule including a series of patients scheduled to undergo procedures in the course of a number of hours, a day, a week, and so on or any time period therebetween, may be inputted into the system and the system may store patient information for the time period necessary to complete the procedures scheduled. As above, patient data for the schedule may be provided in advance of completion of the patient schedule, or the system may retrieve patient information from electronic patient archives.

The system may further be configured to run a self-check to determine, for example, the level of various fluids in the system, including the amount of radiopharmaceutical remaining, the amount of medical fluid remaining, the amount of the other pharmaceutical remaining, the amount of waste, and the like and combinations thereof. In some embodiments, the system may be configured to provide a warning when insufficient radiopharmaceutical, other pharmaceutical, or medical fluid remains to complete a procedure, or the waste receptacle reaches a particular level of fullness. The system may further provide information regarding the internal pressure, temperature of the system or portions thereof, computer system, power supply, battery life, pump status, motor status, the number of protocols carried out with an MPDS, and the like and combinations thereof. In some embodiments, the system may be configured to provide an audible or visual warning when the system pressure drops below a minimum or rises above a maximum level. The system may also provide warnings if pump fails or the temperature in the calibration chamber or vial holding well reaches a critical level, power is lost, or other interruption in the procedure is identified. In certain embodiments, the system may automatically stop without input from the operator when critical parameters have been reached to avoid injury to the patient.

In some embodiments, the system may be configured to administer a single radiopharmaceutical composition, and in other embodiments the system may be configured to deliver two or more different radiopharmaceuticals. In embodiments in which the system is configured to deliver multiple radiopharmaceuticals, the system may allow the operator to switch configurations depending on the intended procedure. The amount of radiopharmaceutical delivered by the system may vary among embodiments and based on the protocol being used. Generally, a physician or other qualified medical personnel can determine an appropriate amount of the radiopharmaceutical to be delivered to a particular patient using metrics regarding the patient known in the art. Because of the flexibility of the system, any amount of radiopharmaceutical can be delivered.

The system may likewise be configured to deliver any other pharmaceutical composition alone or in addition to the radiopharmaceutical. For example, in various embodiments, the system may be configured to administer stress agent such as, but not limited to, IV dobutamine, IV dipyridiamole (Persantine), IV adenosine (Adenoscan), IV lexiscan (Regadenoson), and the like and combinations thereof. In other embodiments, the pharmaceutical agent may reduce vasodilation such as, for example, IV aminophylline. The amount of other pharmaceutical or stimulant delivered by the system may vary among embodiments and based on the protocol being used, and a physician or other qualified medical personnel can determine an appropriate amount of the pharmaceutical to be delivered based on patient metrics known in the art. Because of the flexibility of the system, any amount of other pharmaceutical can be delivered.

The system may be configured to deliver the radiopharmaceutical and other pharmaceutical or stimulant separately or simultaneously depending on the protocol used. For example, in some embodiments, the radiopharmaceutical may be administered to the patient followed by the administration of the other pharmaceutical or stimulant, and in other embodiments, the radiopharmaceutical and other pharmaceutical or stimulant may be administered simultaneously by the system. In still other embodiments, the other pharmaceutical may be administered and the radiopharmaceutical may be delivered at an appropriate time following administration of the other pharmaceutical. For example, in certain embodiments, a stimulant may be administered to a patient, and a radiopharmaceutical may be administered based on real time patient data such as a target heart rate, pulse, and the like. Similarly, the system may be configured to administer additional pharmaceuticals based on real time patient data. For example, if real time patient data indicates that a particular patient metric such as heart rate is too high a depressant may be administered.

Other capabilities and functions not expressly discussed hereinabove or shown in the drawings are of course conceivable in accordance with the embodiments. For example, if the extraction of a dose of the radiopharmaceutical from a vial is interrupted, the system could alert the operator to discard the dose and present a button for that purpose on the GUI.

Figure 5:
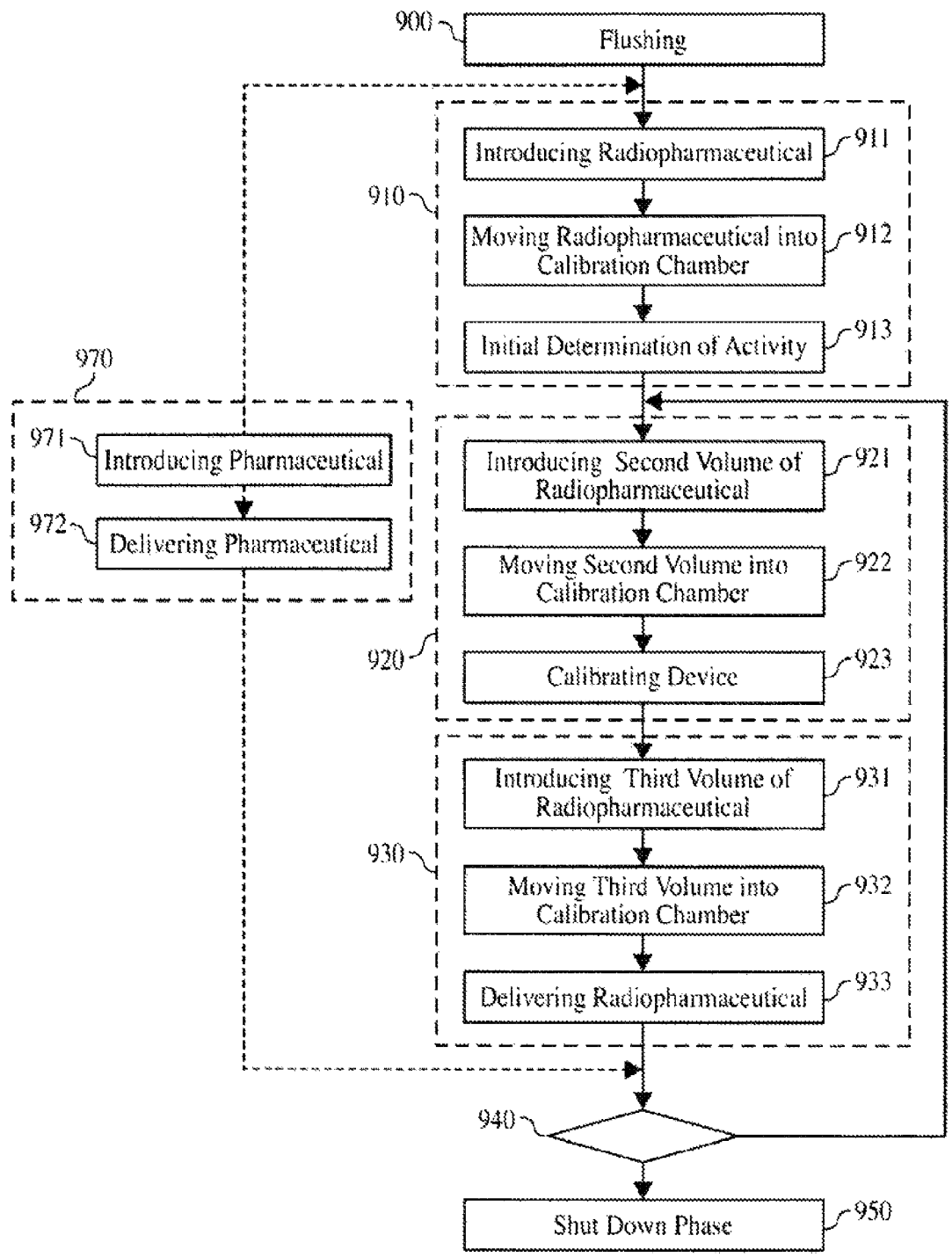
FIG. 5 is flow chart representing exemplary methods for using the radiopharmaceutical delivery system of some exemplary embodiments.

Various embodiments are directed to methods for using the system and devices encompassed by the system. FIG. 5 shows a flow diagram illustrating some exemplary methods of the invention. Generally, the injection procedure can be divided into five phases as represented in the flow chart of FIG. 5: 1) an initialization phase 910, 2) a calibration phase 920, 3) a delivery phase 930, 4) a procedure review phase 940 in which it is determined whether another injection shall be performed and the injection procedure is reinitiated or the injection procedure is complete, and 5) a shutdown phase 950. While the procedure set forth below is directed to delivery of a radiopharmaceutical, embodiments are not limited to delivery of radiopharmaceuticals and similar methods can be carried out for delivery of any other pharmaceutical composition.

In some embodiments, before starting the injection procedure, the operator may determine, i) the desired amount of radiopharmaceutical to be delivered to the patient based on the activity of the radiopharmaceutical, Ar, and ii) the estimated concentration of activity in the vial Cv (i.e., the activity per unit of volume, MBq/ml). These data may be provided to the system controller. In other embodiments, data provided to the controller may further include, the type of radiopharmaceutical provided in the system, patient information including, for example, patient name and vital statistics for the patient, the treating physician, the time of day and/or date, the type or procedure to be performed, the type of procedure and patient information for procedures to be performed before or after the procedure, the name and/or identification number of the operator, a password or other security measure, and the like and combinations thereof. The methods of various embodiments, may include the step of inputting such information before beginning the procedure. In certain embodiments, methods may further include generating a list of procedures to be performed over a time period. While the information provided in such a list may vary, in some embodiments, the list may include patient names, type of procedure, amount of radiopharmaceutical to be delivered to the identified patient, the time necessary of the procedure and/or a projected start time for the procedure, the treating physician, and the like. In particular embodiments, the information required for such a list may be inputted into the system before initiation, and in other embodiments, information for the list may be provided before the initiation of the procedure for each individual patient. In still other embodiments, information for the list may be inputted remotely, and patient information may be provided to the system via an Internet or other network connection that is hardwired or wireless.

Initialization 910 may include any number of steps necessary to prepare the system for delivery of a radiopharmaceutical. In some embodiments, initialization may include the step of filling the system including all tubing and connectors with saline or another medical fluid to remove air from the fluid path set, i.e., flushing the system 900. With reference to FIG. 1, priming can be carried out by any combination of activating of roller pumps A, B, and C. For example, priming may include the steps of activating roller pump A to draw fluid from a medical fluid source positioned at the pharmaceutical source 201 through the confluence 202 and into the third tubing section before being shunted to medical fluid by-pass tubing section 2016 and into the waste receptacle 205 completely filling these sections with medical fluid and removing all air from these sections. The method may further include the step of stopping activation of roller pump A and activating roller pump B to draw fluid from the medical fluid source 203 through the confluence 202, into the third tubing section 2004 through the measurement coil 2008 and waste by-pass tubing section 2014 to the waste receptacle 205 thereby filling these tubing sections with medical fluid. Roller pump B may then be deactivated and the method may include activating roller pump C which will cause medical fluid to be drawn from the medical fluid source 203 through the medical fluid by-pass tubing section 2016 through the confluence 202 and the third tubing section 2004 to the exit port 2006 and into the SPDS 2010. Activation of pump C may completely fill these tubing sections with medical fluid and remove all air from the system. After pump C is deactivated, the fluid path set may be completely filled with medical fluid and all air in the system may be removed.

The radiopharmaceutical source 201 may then be placed in contact with the first tubing section 2000 and pump A may be activated causing radiopharmaceutical to be drawn from the pharmaceutical source 201 through the first tubing section 2000 to the confluence 202. Pump A may then be deactivated. In some embodiments, roller pump B may be activated to flush any pharmaceutical from the confluence before the system is activated for delivery of the pharmaceutical to a patient.

The system being prepared for delivery, the method of various embodiments may include the step of connecting a patient to the system. The step of connecting may be carried out by any means including, for example, introducing a catheter into a patient's vein and attaching an SPDS that is in fluid communication with the exit port 2006 and the fluid path set to the catheter. In other embodiments, the SPDS may be attached to an existing catheter port in the patient's vein. In such embodiments, the SPDS may be flushed and primed with the remainder of the fluid path set to ensure that no air is introduced into the patient's vein during operation of the device. In certain embodiments, roller pump C may be activated to initiate flow of medical fluid to the patient through medical fluid by-pass tubing section 2016 and the third tubing section 2004 after the patient is connected to the device.

Returning to FIG. 5, delivery of the pharmaceutical to the patient can be carried out by introducing a radiopharmaceutical into the system 911. In operation, roller pumps B and C may be deactivated and roller pump A may be activated for a sufficient time period to introduce a first volume of pharmaceutical into the confluence 202 and a first portion of the third tubing section 2004a. The first volume may have a predetermined volume that can vary among embodiments, and the actual amount of radiopharmaceutical in the first volume does not need to be known exactly so long as the activity in the volume is not larger than the total activity to be administered (Ar). The first volume can be delivered by operating roller pump A for a specific time period or number of revolutions known to move the particular volume of pharmaceutical into the first portion of the third tubing section 2004a. Roller pump A may then be deactivated. Moving the radiopharmaceutical into the calibration chamber 912 may be carried out by activating roller pump B for a specific time period or number of revolutions to introduce medical fluid through the confluence 202 and into the first portion of the third tubing section 2004a pushing the first volume of radiopharmaceutical into the measuring coil 2008. Determining an initial activity 913 can be carried out to determine a first measurement of radioactive emissions, A1, using the activity measuring device.

Having made an initial determination of the radioactive emissions of the first volume, $A_1$, the system controller may calculate the missing activity, Am, based on total desired activity, Ar, as shown in Equation 1:

$$Am=Ar-A1 \qquad \text{Eq. 1}$$

In some embodiments, the system may estimate the volume of radiopharmaceutical, Vm, necessary for the missing activity, Am, based on the volume of the first volume. For example, if the first volume had a volume of 1 ml and an A1 that is 50% of Ar, a 1 ml second volume Am may be introduced by activating roller pump A for the same time period or number of revolutions as was used to introduce the first volume to make an Ar dose. Similarly, if a 1 ml first volume results in an A1 that is 75% of Ar, a 0.5 ml second dose may be introduced into the system.

In other embodiments, the concentration of activity in the vial, Cv, can be inputted into the control system by the user during initialization of the system or the Cv can be determined by the system using detectors in the vial well, and this value can then be used to estimate the Vm necessary to achieve the total desired activity, Ar, as shown in Equation 2:

$$Vm=Ar/Cv \qquad \text{Eq. 2}$$

After the estimated remaining volume, Vm, has been determined, the calibration phase 920 may begin. Calibration can be accomplished by introducing a second volume of radiopharmaceutical into the system 921 by activating roller pump A. In some embodiments, the volume of the second volume may equal the estimated missing volume, Vm, and in other embodiments, the volume of the second volume of radiopharmaceutical may be half of the estimated missing volume, Vm. This volume is designated Vc' in Equation 3:

$$Vc'=Vm/2 \qquad \text{Eq. 3}$$

The second volume of radiopharmaceutical may then be introduced into the activity measuring device, 922, by deactivating roller pump A and activating roller pump B to introduce additional medical fluid into the fluid path set.

Calibrating the activity measuring device, 923, can be carried out by taking a second measurement, M2, which corresponds to the radioactive emission of both the first volume V1 of radiopharmaceutical and the second volume of radiopharmaceutical, Vc', because both volumes are present in the tube coil during the measurement. The activity of the second volume, Ac', can be determined by subtracting the activity of the first volume A1 measured in the first measurement M1 from the activity, A2, derived from the second measurement M2. The concentration of radiopharmaceutical in the vial based on the emission, Cs, can be calculated based on the amount of radiopharmaceutical, Vc', introduced into the system in the second volume of radiopharmaceutical, and the activity of these volume of radiopharmaceutical, Ac', as set-forth in Eq. 4:

$$Cs=Ac'/Vc'=(A2-A1)/Vc' \qquad \text{Eq. 4}$$

The system is now calibrated and can deliver an accurate dose, for example in mCi, or in MBq, of radiopharmaceutical based on the volume of radiopharmaceutical introduced into the system.

The additional amount of radiopharmaceutical required for the desired total dose Ar can be determined by determining the amount of activity Ac" required to reach a total activity of Ar as set forth in Eq. 5:

$$Ac''=Ar-A2 \qquad \text{Eq. 5}$$

The volume Vc" required to provide this dose of radiopharmaceutical can then calculated as set forth in Eq. 6:

$$Vc''=Ac''/Cs=(Ar-A2)/Cs=(Ar-A2)/(A2-A1)Vc' \qquad \text{Eq. 6}$$

Having determined the correct amount of radiopharmaceutical to provide the total desired dose Ar, the delivery phase, 930, can be initiated. Delivery can include the steps of introducing a third volume of radiopharmaceutical into the system 931 by activating roller pump A, and pumping the volume, Vc", through the confluence 202 and into the first portion of the third tubing section 2004*a*. The third volume of radiopharmaceutical can then introduced into the activity measuring device, 932, by deactivating roller pump A and activated roller pump B pumping a volume of medical fluid into the system sufficient to allow the third volume of radiopharmaceutical to enter the measurement coil. In some embodiments, the total activity in the measurement coil can be determined (measurement M3) to confirm that the appropriate total dose of radiopharmaceutical, corresponding to the total desired activity Ar, has been introduced into the system and is prepared for delivery 933. If a significant discrepancy is detected, the system can be stopped before the radiopharmaceutical is delivered. In such embodiments, the volume of the tube coil must be large enough to hold all three volumes of radiopharmaceutical. In other embodiments, the third volume of radiopharmaceutical may be pushed past the tubing coil for delivery without further measuring the activity of the radiopharmaceutical.

In some embodiments, the an accurate dose of radiopharmaceutical, Ar, can be obtained and delivered to a patient by introducing a first volume of radiopharmaceutical, V1, into the activity measuring device, 932, and measuring the activity of the first volume of radiopharmaceutical, AV1. The volume of radiopharmaceutical necessary to produce the total dose may be determined based on the activity of the first volume as set forth in Eq. 7:

$$AV2=Ar-AV1 \qquad \text{Eq. 7.}$$

Where AV2 is the necessary activity for a second volume of radiopharmaceutical V2, and the volume V2 required to provide this dose of radiopharmaceutical can then calculated as set forth in Eq. 8:

$$V2=AV2/Cs \qquad \text{Eq. 8}$$

where Cs is the concentration of radiopharmaceutical in the vial based on the emission determined as described herein. The second volume, V2, of radiopharmaceutical may be introduced into the system to create the total desired dose of radiopharmaceutical, Ar, to be delivered to the patient. This two volume method may be carried out after calibration using the three volume method described above, and results in delivery of a total desired does with the same accuracy as the three volume method.

The total desired dose of radiopharmaceutical, Ar, being introduced into the system, the radiopharmaceutical can be delivered to the delivery tube set, 933 by activating roller pump C causing medical fluid to flow through the medical fluid by-pass tubing section 2016 into the confluence 202 and through the third tubing section 2004 and exit port into the SPDS and to the patient. Thus, all liquid in the measurement coil can be flushed to the patient, and exactly the required dose of radioactivity is delivered to the patient.

In various embodiments, the method presented above may further include the step of delivering a dose of a pharmaceutical agent to the patient, 970. This step can be carried out at any point in the process and may include the steps of introducing a volume of pharmaceutical agent sufficient to elicit the desired effect, and delivering the pharmaceutical agent to the patient 972. In some embodiments, the amount of pharmaceutical agent to be delivered can be determined by a physician or other medical professional. This amount can be provided in a single use syringe provided with an appropriate volume of pharmaceutical agent for delivery to a single patient. In such embodiments, the system may be configured to depress the plunger completely when the step of delivering the pharmaceutical agent 972 is initiated. In other embodiments, the amount of pharmaceutical agent may be provided in a multiuse syringe including a sufficient amount of radiopharmaceutical to be delivered to more than one patient. In such embodiments, a motor, for example, may be used to discharge an appropriate amount of pharmaceutical agent for each individual patient. The user can control the amount of radiopharmaceutical administered by controlling the motor, or providing instructions to the control system to discharge an appropriate amount of pharmaceutical agent.

The pharmaceutical agent can be introduced into the system at any point within the flow path. For example, in some embodiments, the pharmaceutical agent may be introduced into the SPDS at either the proximal or distal end of the delivery tube, and in other embodiments, the pharmaceutical agent can be introduced into MPDS either before or after the tube coil. As illustrated in FIG. 5, the step of introducing the pharmaceutical agent into the system may be carried out after flushing the system 900 and before the radiopharmaceutical delivery procedure has been initiated or the step of introducing the pharmaceutical agent into the system can be carried out after the radiopharmaceutical has been delivered to the patient and before the system is shut down 950. In still other embodiments, the pharmaceutical agent can be introduced into the system simultaneously with the radiopharmaceutical and both compositions can be delivered to the patient at the same time.

In some embodiments, another injection of the radiopharmaceutical and/or another injection of pharmaceutical agent may be delivered to the same or a different patient. In such embodiments, procedure may continue by repeating the delivery phases 930 alone, or the calibration phase 920 and delivery phase 930 when additional radiopharmaceutical is required, and/or the pharmaceutical agent delivery phase 970, when additional pharmaceutical agent is required. In various embodiments, the initialization phase 910 may not be repeated, since the tube coil 910 has been flushed with saline, and the radiopharmaceutical extends to confluence 202. Moreover, because no activity is present in the measurement coil section, Al, in the above calculations, can be set to zero, and Am and Ar are equal. In the event that no further injections are necessary, the procedure maybe terminated using a shutdown protocol, which may include one or more steps of flushing system with a medical fluid.

In still other embodiments, another injection of pharmaceutical agent may be carried out by providing a single dose having the appropriate radioactive emission, Ar. In such embodiments, the control system may determine the total volume of radiopharmaceutical administered by determining the total volume V1, Vc', and Vc" and delivering the total volume, Vr, of radiopharmaceutical into the device in a single dose. The radioactive emissions of the total volume, Vr, may be confirmed in the measurement coil before the dose is delivered to the patient. Thus, in some embodiments, the initialization 910 and calibration 920 phases may be skipped after an initial initialization and calibration has been carried out.

The systems, methods, and devices described above may include a number of inherent safety features. For example, redundancy in the operation of the device may reduce the possibility that more than the desired dose of radiopharmaceutical will be delivered to the patient, even in the event of failure of one component, such as a pump. In particular, only the dose of radiopharmaceutical in the measurement coil will be delivered to the patient because there is no direct connection from the vial and the fluid delivery set. Additionally, sequential measurement of activity within the measurement coil allows the radioactive dose of radiopharmaceutical to be determined before the complete dose is introduced into the system. Thus, measurement M3 confirms that the correct amount of radiopharmaceutical is present in the tube coil before the radiopharmaceutical is delivered. If significant discrepancies are detected between the expected result and the actual measurement, procedure can be terminated, and/or the user will be notified of the discrepancy using, for example, an audible or visible alarm.

The methods described above may include any number of additional steps including, for example, replacing the fluid path set, placing the waste receptacle into the waste receptacle well, placing tube coil into activity measuring device, placing tubing into operative connection with pump, placing the tubing into operative connection tubing holder, placing a spike or cannula into fluid connection with radiopharmaceutical source or vial, placing tubing into operative connection with pinch valve, and placing tubing into operative connection with air detectors, mounts, and other devices, hanging a medical fluid source on a hook, mounting on fluid delivery system, and combinations thereof. The method may further include priming the system by flushing with medical fluid, connecting the SPDS with the MPDS, priming the SPDS to provide a wet connection at the patient end.

Additional embodiments are directed to a method for estimating the flow rate of the device using, for example, flow rate sensors, pressure sensors, or the change of activity (slope) of the radiopharmaceutical. In embodiments in which the activity of the radiopharmaceutical is used to determine flow rate, a known volume of the radiopharmaceutical can be pumped into and out of the activity measuring device by pumping additional fluid into the third and fourth tubing sections. The activity of the radiopharmaceutical in the activity measuring device can be measured repeatedly during this process and a slope of the radioactive emissions can calculated from the measured activity values over time. Based on the slope of the emitted radiation and the volume of the activity measuring device, the average rate at which the radiopharmaceutical is replaced by saline can be calculated which corresponds to the flow rate of the fluid in the device. Because the radiopharmaceutical and chamber materials may be chosen such that radioactive emissions from the radiopharmaceutical penetrate the walls of the activity measuring device before being measured, it is possible to measure the flow rate of the fluid without placing mechanical measuring devices in the fluid stream.

Similarly, the flow rate of a radiopharmaceutical to a patient and the location of the radiopharmaceutical within the MPDS can be determined. In particular, the activity in the chamber (Ac) in the activity measuring device and activity in the tubing (At) at the beginning of the procedure can be measured directly. Based on these data, the activity per unit concentration (e.g., MBq/ml or mCi/ml) can be determined for the vial as a whole. In some embodiments, the decay rate for the radioactive tag can be used to determine the activity of the radiopharmaceutical remaining in the vial. In still other embodiments, the total time for the infusion attempt, and the volume of tubing between the activity measuring device and the end of the patient line can be used in conjunction with the data described above to determine precisely the amount of radiopharmaceutical administered to the patient.

Once the average flow rate of the radiopharmaceutical through the MPDS is determined, this information can be used to determine the location or distribution of the first volume of radiopharmaceutical, the second volume of radiopharmaceutical, and/or the third volume of radiopharmaceutical within the system. Additionally the average flow rate along with fluid mechanical properties of the tubing such as diameter and surface treatment, can be used to determine the location of the leading edge and the trailing edge of the radiopharmaceutical volume. By knowing the location of the radiopharmaceutical within the fluid path set, system parameters can be adjusted to ensure that the injection is fully completed and the radiopharmaceutical dose and pharmaceutical agent are completely administered.

The invention claimed is:

1. A device for delivering a pharmaceutical, the device comprising:
   two or more roller pumps comprising at least a first roller pump and a second roller pump; and
   a fluid path set wherein a portion of the fluid path set is reversibly received by the two or more roller pumps, the fluid path set comprising:
   a first tubing section fluidly connecting a pharmaceutical source to a confluence, wherein a flow of fluid through the first tubing section is controlled by the first roller pump;
   a second tubing section fluidly connecting a source of medical fluid to the confluence, wherein a flow of fluid through the second tubing section is controlled by the second roller pump;
   a third tubing section fluidly connecting the confluence to an exit port;
   a fourth tubing section fluidly connecting the third tubing section or a portion thereof to a waste receptacle; and
   a waste by-pass tubing section fluidly connecting an upstream portion of the fourth tubing section with a downstream portion of the fourth tubing section, wherein a flow of fluid through the waste by-pass tubing section is controlled by the second roller pump.

2. The device of claim 1, further comprising a delivery tubing section for delivering fluid to a patient, wherein the delivery tubing section is reversibly connected to the exit port.

3. The device of claim 1, wherein the two or more roller pumps further comprise a third roller pump configured to control a flow of fluid through the fourth tubing section.

4. The device of claim 3, further comprising a medical fluid by-pass tubing section fluidly connecting an upstream portion of the second tubing section to a downstream portion of the second tubing section.

5. The device of claim 4, wherein a flow of fluid through the medical fluid by-pass tubing section is controlled by the third roller pump.

6. The device of claim 5, wherein operating the third roller pump causes fluid to flow from the source of medical fluid through the medical fluid by-pass tubing section to the confluence, and into the third tubing section to the exit port.

7. The device of claim 4, wherein the medical fluid by-pass tubing section is fluidly connected to the upstream portion of the second tubing section by a first T-joint, and the medical fluid by-pass tubing section is fluidly connected to the downstream portion of the second tubing section by a second T-joint.

8. The device of claim 4, wherein the medical fluid by-pass tubing section is fluidly connected to the confluence.

9. The device of claim 1, wherein a first T-joint connects the third tubing section to the fourth tubing section.

10. The device of claim 1, wherein the waste by-pass tubing section is fluidly connected to the upstream portion of the fourth tubing section by a first T-joint, and the waste by-pass tubing section is fluidly connected to the downstream portion of the fourth tubing section by a second T-joint.

11. The device of claim 1, wherein fluid from the source of medical fluid can flow through the second tubing section, the confluence, the third tubing section, and into the waste receptacle through the waste by-pass tubing section.

12. The device of claim 1, further comprising an activity measuring device disposed between a first portion of the third tubing section and a second portion of the third tubing section.

13. The device of claim 12, wherein the activity measuring device comprises a measurement coil.

14. The device of claim 12, wherein the activity measuring device measures radioactivity.

15. The device of claim 1, further comprising one or more check valves.

16. The device of claim 1, wherein the confluence comprises one or more check valves.

* * * * *

UNITED STATES PATENT AND TRADEMARK OFFICE
CERTIFICATE OF CORRECTION

PATENT NO. : 9,433,728 B2
APPLICATION NO. : 13/783213
DATED : September 6, 2016
INVENTOR(S) : Marsh Page 1 of 1

It is certified that error appears in the above-identified patent and that said Letters Patent is hereby corrected as shown below:

On the Title Page
In item (57), under "ABSTRACT", in Column 2, Line 4, delete "confidence," and insert -- confluence, --, therefor.
In item (57), under "ABSTRACT", in Column 2, Line 8, delete "describe." and insert -- described. --, therefor.

In the Specification
In Column 5, Line 29, delete "exit port 2004b" and insert -- exit port 2006 --, therefor.
In Column 9, Line 21, delete "and fourth" and insert -- and --, therefor.
In Column 9, Line 44, delete "a the" and insert -- the --, therefor.
In Column 9, Line 50, delete "device" and insert -- device. --, therefor.
In Column 11, Line 37, delete "Dipyridiamole" and insert -- Dipyridamole --, therefor.
In Column 12, Line 10, delete "0 5" and insert -- 0.5 --, therefor.
In Column 12, Line 12, delete "revolution." and insert -- a revolution. --, therefor.
In Column 15, Line 44, delete "patients" and insert -- patient --, therefor.
In Column 16, Line 34, delete "dipyridiamole" and insert -- dipyridamole --, therefor.
In Column 18, Line 65, delete "2004apushing" and insert -- 2004a pushing --, therefor.
In Column 20, Line 10, delete "Vc"," and insert -- Vc", --, therefor.
In Column 21, Line 1, delete "effect," and insert -- effect 971, --, therefor.
In Column 21, Line 47, delete "tube coil 910" and insert -- tube coil 410 --, therefor.

Signed and Sealed this
Third Day of January, 2017

Michelle K. Lee
*Director of the United States Patent and Trademark Office*